(12) United States Patent
Matsushita et al.

(10) Patent No.: US 6,293,937 B2
(45) Date of Patent: Sep. 25, 2001

(54) TRUNKS-TYPE DISPOSABLE PANTS

(75) Inventors: Michiyo Matsushita; Takeshi Hanajiri, both of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/785,638

(22) Filed: Feb. 16, 2001

(30) Foreign Application Priority Data

Feb. 18, 2000 (JP) .................................................. 12-046767

(51) Int. Cl.$^7$ .................................................. A61F 13/72
(52) U.S. Cl. .................. 604/396; 604/392; 604/393; 604/394; 604/395; 604/385.19; 604/348; 604/402
(58) Field of Search .................. 604/392–396, 604/402, 385.19, 348

(56) References Cited

U.S. PATENT DOCUMENTS

| | | | |
|---|---|---|---|
| 1,833,960 | * | 12/1931 | Alsop . |
| 5,062,840 | * | 11/1991 | Holt et al. .......................... 604/385.1 |
| 5,176,672 | * | 1/1993 | Bruemmer et al. ............... 604/385.1 |
| 5,397,318 | * | 3/1995 | Dreier ................................ 604/385.2 |
| 5,853,403 | * | 12/1998 | Tanzer et al. ...................... 604/385.1 |
| 6,133,501 | * | 10/2000 | Hallock et al. ...................... 604/369 |

FOREIGN PATENT DOCUMENTS 6-63072    3/1994    (JP) .

* cited by examiner

Primary Examiner—John G. Weiss
Assistant Examiner—Michael Bogart
(74) Attorney, Agent, or Firm—Baker & Daniels

(57) ABSTRACT

Trunks-type disposable pants that include a pair of inner sheets and a pair of outer sheets. The inner sheets have cutouts depressed from the upper ends toward the lower ends and liquid-absorbent panels attached to opposed surfaces of the inner sheets in the vicinity of the respective cutouts. The opposed surfaces of the inner sheets may be bonded together by means of bond lines extending in parallel to the cutouts and partially extending below the liquid-absorbent panels. Opposed surfaces of the inner sheets and the outer sheets are bonded together along the front and rear side portions of these sheets.

6 Claims, 8 Drawing Sheets

TRUNKS-TYPE DISPOSABLE PANTS

BACKGROUND OF THE INVENTION

This invention relates to trunks-type disposable pants.

Japanese Patent Application Publication No. 1994-63072A describes trunks-type disposable pants made by a process comprising steps of placing separately formed with front and rear bodies, bonding these front and rear bodies along bond lines extending on crotch regions of these bodies so as to describe curves being convex upward and attaching a longitudinally larger liquid-absorbent panel to the inner surface of the crotch region. Excretion is absorbed by the liquid-absorbent panel attached to the crotch region.

In the pants disclosed in the Gazette, the longitudinally larger liquid-absorbent panel has a desired width dimension and attached to the crotch region so as to extend in horizontal direction. Transversely opposite side edges of the panel are compressed between thighs of a wearer and these side edges may give the wearer a feeling of incompatibility as the pants are put on the wearer's body. In addition, these side edges have no barriers to prevent excretion spread over the upper surface of the panel from leaking through gap defined between both sides of the crotch region and the wearer's thighs.

SUMMARY OF THE INVENTION

It is an object of this invention to provide trunks-type disposable pants designed so that excretion leak possibly occurring from both sides of a crotch region is reliably avoided without giving a wearer a feeling of incompatibility.

According to this invention, there is provided trunks-type disposable pants having a waist-opening ay its top and a pair of leg-openings ay its bottom wherein the waist-opening is provided along its peripheral edge having an elastic stretchability circumferentially of the waist-opening.

The trunks-type disposable pants further comprises a pair of inner sheets confronting each other and a pair of outer sheets lying outside the inner sheets, the inner sheets as well as the outer sheets being contoured by upper and lower ends transversely extending in parallel to each other, respectively, and front and rear side portions longitudinally extending in parallel to each other, respectively, the inner sheets are formed between their front and rear side portions with cutouts depressed from the upper ends toward the lower ends and provided with mat-like liquid-absorbent panels attached to opposed surfaces of the inner sheets so that the opposed surfaces of the inner sheets are bonded together by means of bond lines extending in parallel to the cutouts and partially extending below the liquid-absorbent panels, and opposed surfaces of the inner sheets and the outer sheets are bonded together along the front and rear side portions of these sheets.

The trunks-type disposable pants according to this invention has a simplified construction such that the inner sheets are placed upon each other and the opposed surfaces of these inner sheets are bonded together while the respective inner sheets are placed upon the respectively adjacent outer sheets and the opposed surfaces of respective pairs of the adjacent inner and outer sheets are bonded together. Such simplified construction facilitates the pants to be made and is suitable for disposable sanitary article.

With the novel pants having the side sheets bonded to the inner sheets in the vicinity of their bottom sides, the side sheets and the regions in the opposed surfaces of the inner sheets extending from the bottom sides to the bond lines are expanded outward transversely of the pants as the elastic members attached to the respective side sheets contract. Consequently, these sheets form a pocket opening upwardly of the pants. The pocket includes therein the liquid-absorbent panels. The side sheets and the inner sheets define the barriers so that the amount of excretion discharged into the pocket is absorbed by the panels and the barriers prevent any leak of the excretion from possibly occurring in the vicinity of the crotch region.

In the pants having the elastic members bonded to the respective inner sheets in the vicinity of the bottom sides thereof, the regions in the opposed surfaces of the inner sheets extending from the bottom sides to the bond lines are expanded outward transversely of the pants as the elastic members bonded to the inner sheets contract. Consequently, the inner sheets form the pocket opening upwardly of the pants. The pocket includes therein the liquid-absorbent panels and the respective inner sheets define barriers functioning to prevent any amount of the excretion having been discharged into the pocket and absorbed by the panels from leaking from the crotch region.

The panels extend in parallel to the inner sheets substantially in the vertical direction and therefore are less bulky in the crotch region than when these panels extend in the horizontal direction. In this manner, it is not apprehended that the panels give the wearer a feeling of incompatibility.

The novel pants achieve a substantially higher bonding strength as measured circumferentially of the pants than that achieved by the pants in which the opposed surfaces are not bonded together along the regions. This is because, according to this invention, the opposed surfaces of the inner sheets are bonded together along regions of the front and rear side portions extending in the vicinity of the respective upper ends of said inner sheets.

DETAILED DESCRIPTION OF THE PREFERRED EMBODIMENTS

Details of disposable pants of trunks-type according to this invention will be more fully understood from the description given hereunder with reference to the accompanying drawings.

Figure 1:
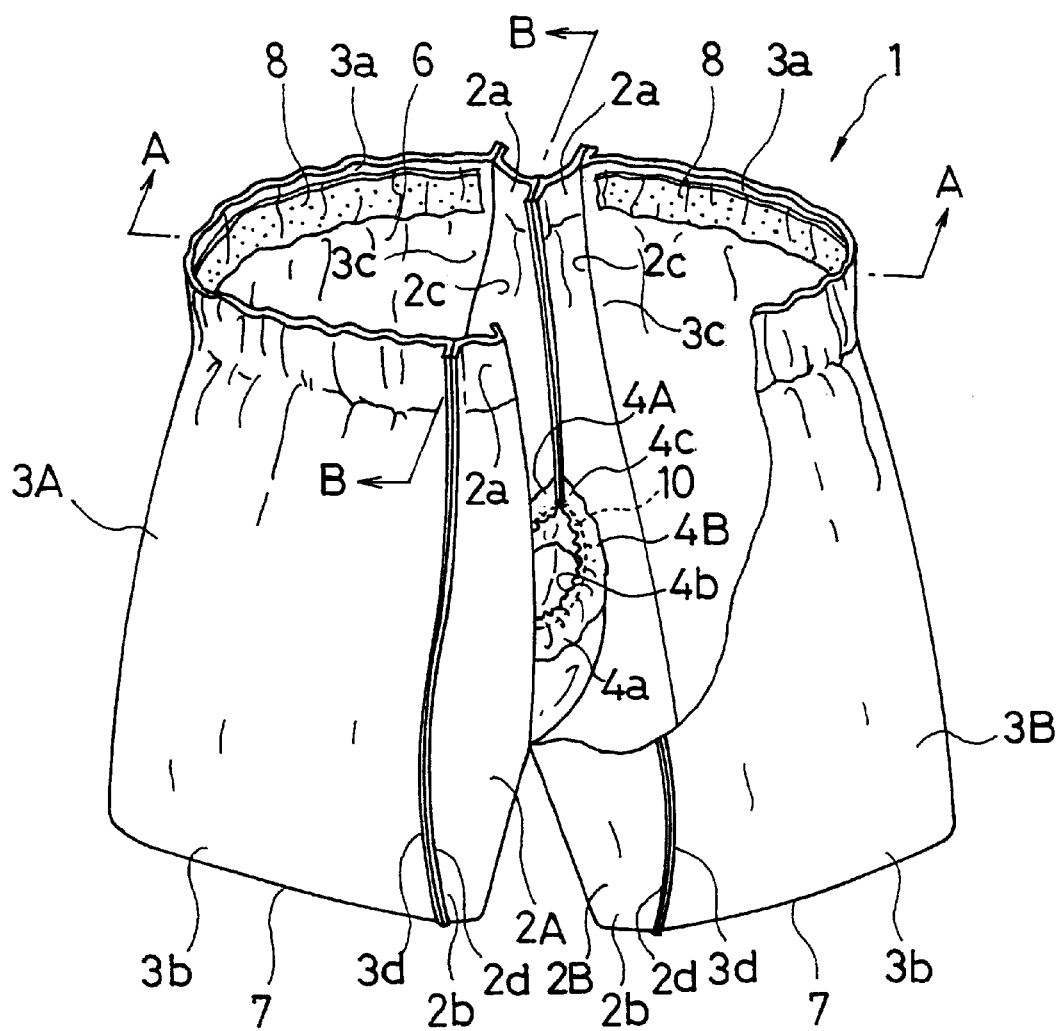
FIG. 1 is a perspective view showing one embodiment of a trunks-type disposable pants according to this invention as viewed from the front.
Figure 2:
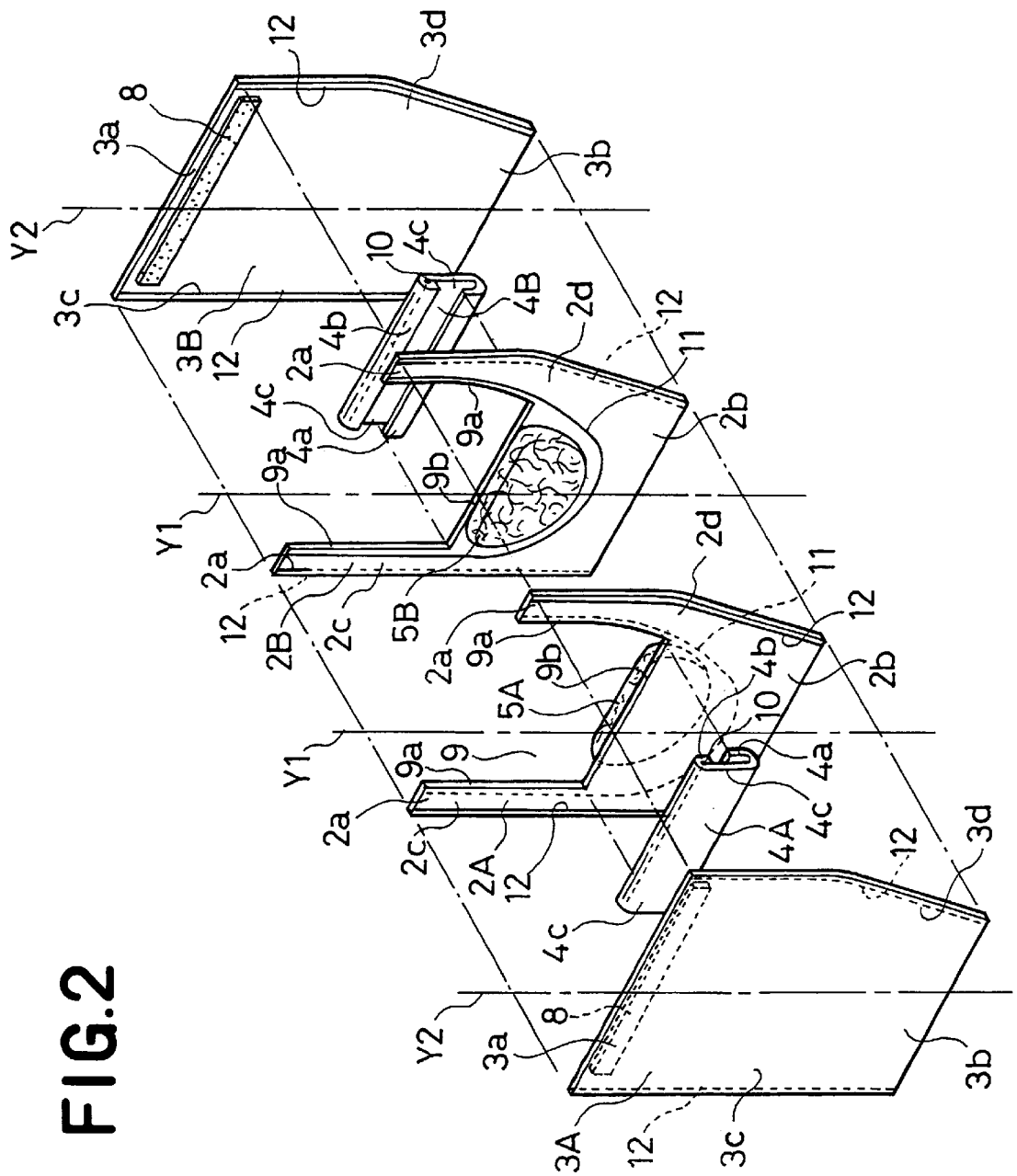
FIG. 2 is an exploded perspective view showing the pants of FIG. 1.

FIG. 1 is a perspective view showing disposable pants 1 as partially broken away and FIG. 2 is an exploded perspective view showing the pants of FIG. 1. In FIG. 2, a pair of inner sheets 2A, 2B are opposed to each other symmetrically with respect to a plane and a pair of outer sheets 3A, 3B are arranged outside the respective inner sheets 2A, 2B so as to be opposed to each other also with respect to a plane. Liquid-resistant side sheets 4A, 4B are interposed between the inner and the outer sheets 2A, 2B; 3A, 3B, respectively.

In addition to these pair of symmetric inner sheets 2A, 2B, pair of symmetric outer sheets 3A, 3B and pair of liquid-resistant side sheets 4A, 4B, the pants 1 further comprise a pair of mat-like liquid-absorbent panels 5A, 5B.

In the pants 1, the inner sheets 2A, 2B and the outer sheets 3A, 3B define together a waist-opening 6 along a top of the pants 1 and a pair of leg-openings 7 along a bottom of the pants 1. The waist-opening 6 is provided along its peripheral edge with a film-like elastically stretchable member 8 bonded with tension thereto so as to extend circumferentially of the pants The inner sheets 2A, 2B are contoured by upper and lower ends 2a, 2b extending in parallel to each other transversely of the pants 1 and front and rear side portions 2c, 2d extending in parallel to each other longitudinally of the pants 1. The inner sheets 2A, 2B are formed between the front and rear side portions 2c, 2d with a cutout 9 depressed from the upper end 2a toward the lower end 2b. This cutout 9 is contoured by opposite sides 9a of the inner sheets 2A, 2B extending longitudinally thereof and a bottom side 9b of the inner sheet 2A, 2B transversely extending between respective lower ends of the opposite sides 9a.

In the vicinity of the bottom sides 9b of the inner sheets 2A, 2B, the side sheets 4A, 4B transversely extend above the panels 5A, 5B. The rear side edge 2d of the inner sheets 2A, 2B gets nearer, describing a circular arc, to a longitudinal center line Y1 bisecting a dimension between the front side portion 2c and the rear side portion 2d as the rear side edge 2d extends from the upper end 2a toward the lower end 2b.

The panels 5A, 5B are placed in a region surrounded by the front and rear side portions 2c, 2d, the lower end 2b and the bottom side 9b of the inner sheets 2A, 2B and bonded to a surface of the sheets 2A, 2B opposed to the panels 5A, 5B.

The side sheets 4A, 4B are of a rectangular shape which is transversely longer and has a fixed end 4a bonded to the inner sheets 2A, 2B in the vicinity of its bottom side 9b, a free end 4b extending across the cutout 9 above the fixed end 4a, and transversely opposite fixed ends 4c longitudinally extending in parallel to the front and rear side portions 2c, 2d of the inner sheets 2A, 2B and bonded to the inner sheets 2A, 2b in the vicinity of its opposite sides 9a. The free end 4b is provided with a transversely extending elastically stretchable member 10 bonded with tension thereto so that the member 10 is covered with a portion of the free end 4b.

The outer sheets 3A, 3B are contoured by upper and lower ends 3a, 3b transversely extending in parallel to each other and front and rear side edges 3c, 3d longitudinally extending in parallel to each other. The rear side edge 3d of the outer sheets 3A, 3B gets nearer, describing a circular arc, to a longitudinal center line Y2 bisecting a dimension between the front side edge 3c and the rear side edge 3d as the rear side edge 3d extends from the upper end 3a toward the lower end 3b. Surface of the outer sheets 3A, 3B opposed to the inner sheets 2A, 2B are provided along upper end 3a with a transversely extending elastic member 8 bonded thereto.

To assemble the components illustrated by FIG. 2 in the exploded perspective view and thereby to obtain the pants 1, the inner sheets 2A, 2B are placed upon each other with the respective center lines Y1 brought in line with each other and then the opposed surfaces thereof are continuously or intermittently bonded to each other along bond lines 11. These bond lines 11 extend in parallel to the cutouts 9, describing circular arcs, from the upper ends 2a toward the lower ends 2b of the sheets 2A, 2B, respectively. The portions of the bond lines 11 describing the circular arcs extend between the panels 5A, 5B and the lower ends 2b of the sheets 2A, 2B.

After the opposed surfaces of the inner sheets 2A, 2B have been bonded to each other, the respective fixed ends 4a of the side sheets 4A, 4B are partially folded back to respective inner surfaces of the side sheets 4A, 4B and these fixed ends 4a are bonded to respective outer surfaces of the sheets 2A, 2B in the vicinity of their respective bottom sides 9b. At the same time, the transversely opposite ends 4c also are bonded to the sheets 2A, 2B in the vicinity of their opposed sides 9a with the elastic members 10 being kept under tension.

The inner sheets 2A, 2B and the outer sheets 3A, 3B are placed upon one another, respectively, with the center lines Y1, Y2 of these inner and outer sheets 2A, 2B; 3A, 3B brought in line with one another, respectively. Thereupon, the upper and lower ends 2a, 3a; 2b, 3b as well as the front and rear side portions 2c, 3c; 2d, 3d of the inner and outer sheets 2A, 2B; 3A, 3B are also brought in lines, respectively, with one another.

The inner and outer sheets 2A, 3A have their surfaces opposed to each other continuously or intermittently bonded to each other by means of bond lines 12 extending along the front and rear side portion 2c, 2d; 3c, 3d, respectively. Similarly, the inner and outer sheets 2B, 3B have their surfaces opposed to each other continuously or intermittently bonded to each other by means of bond lines 12 extending along the front and rear side portions 2c, 2d; 3c, 3d, respectively.

Figure 3:
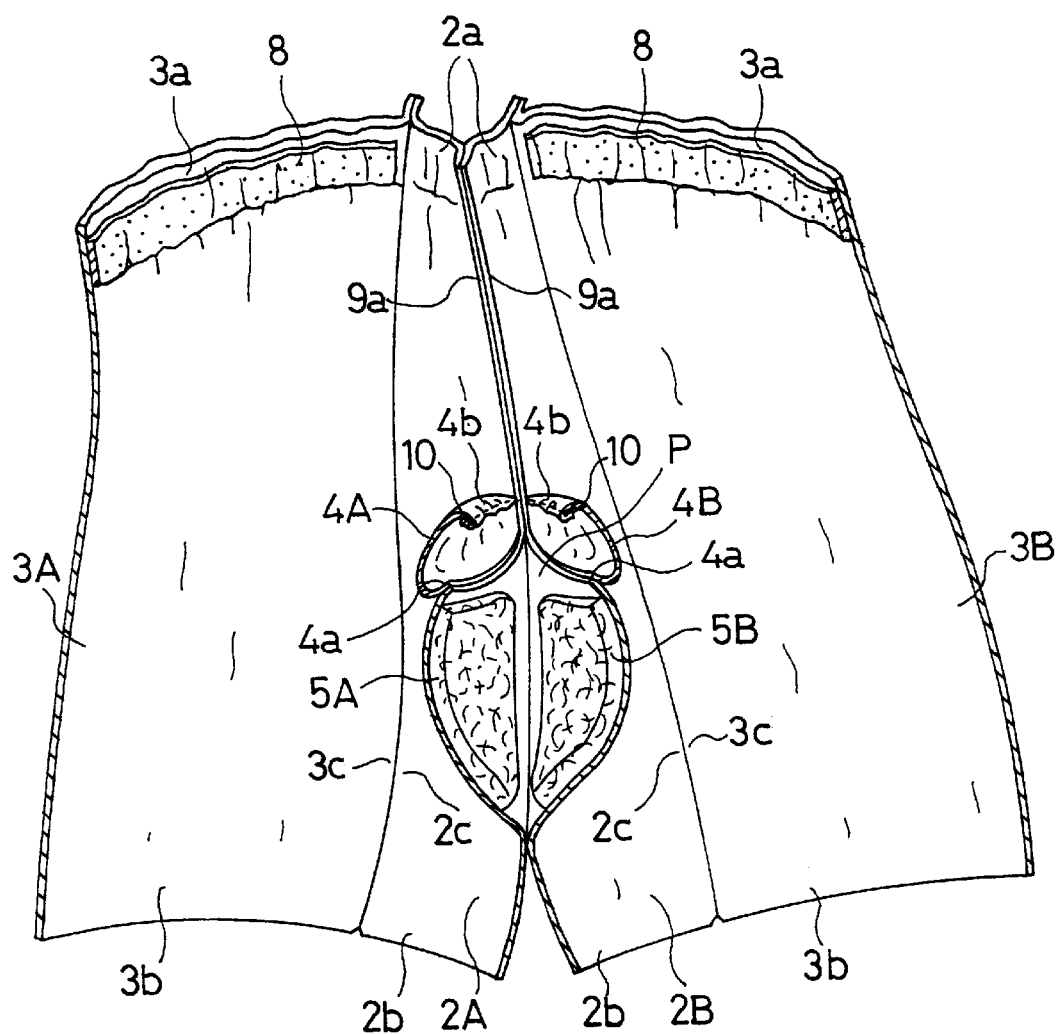
FIG. 3 is a perspective view showing the pants of FIG. 1 as viewed in a section taken along line A—A in FIG. 1.
Figure 4:
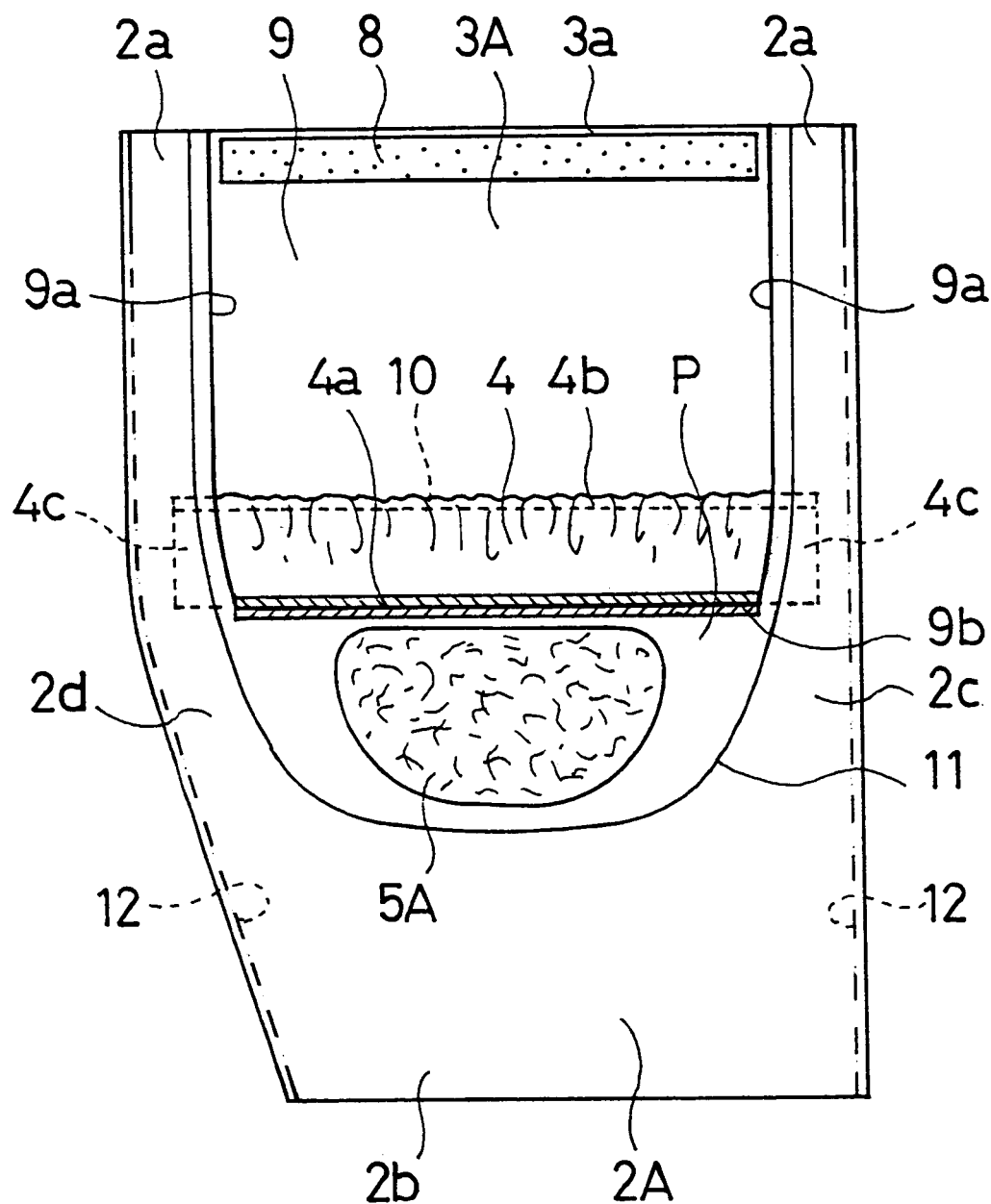
FIG. 4 is a sectional view showing the pants of FIG. 1 as taken along line B—B.

FIG. 3 is a perspective view showing the pants of FIG. 1 as viewed in a section taken along line A—A in FIG. 1 and FIG. 4 is a sectional view showing the pants of FIG. 1 as taken along line B—B. Of the inner sheets 2A, 2B placed upon each other, the respective opposed sides 9a are placed upon each other so as to be oriented inwardly of the pants 1. The inner sheets 2A, 2B and the outer sheets 3A, 3B have their front and rear side portions 2c, 2d; 3c, 3d placed upon one another so as to be oriented outwardly of the pants 1.

In the pants 1 assembled, the respective side sheets 4A, 4B as well as the opposed surfaces of the inner sheets 2A, 2B extending from their bottom sides 9b to the respective bond lines 11 expand outward transversely of the pants 1 as the elastic members 10 bonded with tension to the respective free ends 4b of the side sheets 4A, 4B contract so that these sheets 2A, 2B, 4A, 4B form a pocket P opening upwardly of the pants In the pants 1 assembled, the respective fixed ends 4a of the side sheets 4A, 4B have been folded back toward the inner surfaces thereof and bonded to the respective outer surfaces of the inner sheets 2A, 2B. The respective free ends 4b of the side sheets 4A, 4B are biased to tilt outward transversely of the pants 1 and thereby to open the pocket P.

The side sheets 4A, 4B and the inner sheets 2A, 2B forming the pocket P serve as barriers of the pocket P. Excretion discharged into the pocket P is absorbed by the panels 5A, 5B lying within the pocket P. The barriers function to prevent excretion leak from occurring in the vicinity of a crotch region. The panels 5A, 5B extend substantially in vertical direction in parallel to the inner sheets 2A, 2B and, in a wearer's crotch region, are less bulky than in the case of the panels 5A, 5B extending in horizontal direction. Thus, it is not apprehended that these panels SA, 5B might give the wearer a feeling of incompatibility.

Figure 5:
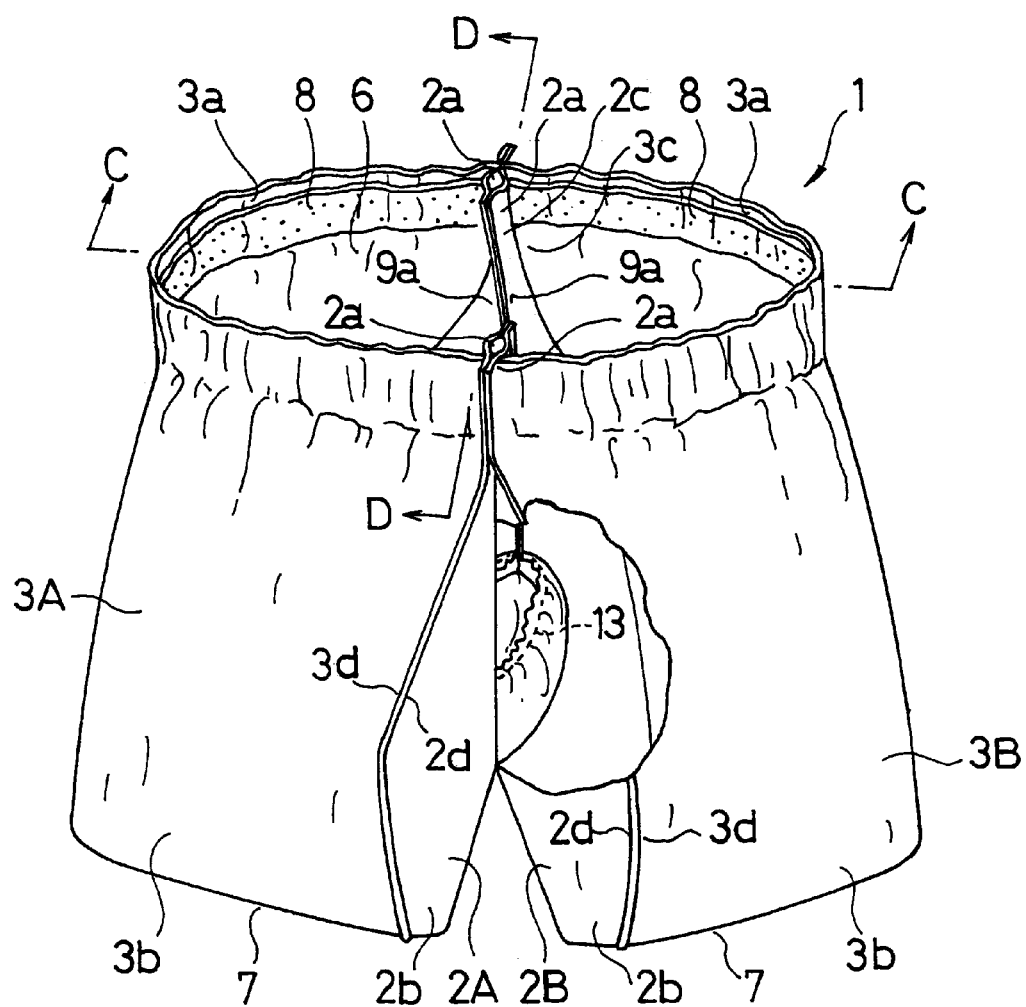
FIG. 5 is a perspective view showing the trunks-type disposable pants as one embodiment of this invention different from that of FIG. 1 as viewed from the front.
Figure 6:
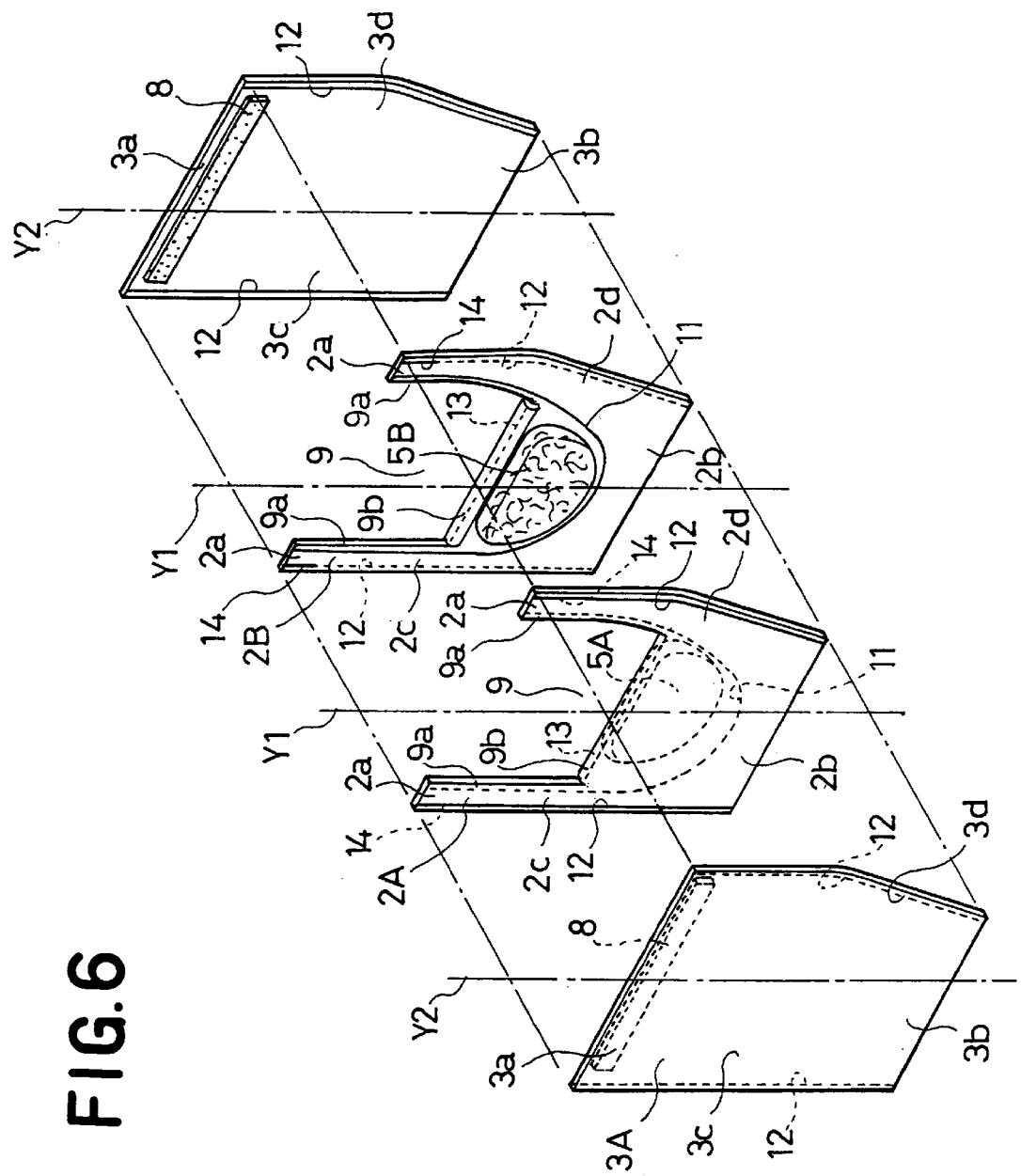
FIG. 6 is an exploded perspective view showing the pants of FIG. 5.

FIG. 5 is a perspective view showing the trunks-type disposable pants 1 as a specific embodiment of this invention different from that of FIG. 1 as viewed from the front and FIG. 6 is an exploded perspective view showing the pants 1 of FIG. 5. Referring to FIG. 6, the inner sheets 2A, 2B are symmetrically opposed to each other with respect to a plane and the outer sheets 3A, 3B are also symmetrically opposed to each other with respect to a plane outside the inner sheets 2A, 2B.

The pants 1 according to this alternative embodiment comprise a pair of inner sheets 2A, 2B, a pair of outer sheets 3A, 3B and a pair of mat-like liquid-absorbent panels 5A, 5B so as to define a waist-opening 6 at a top of the pants 1 and a pair of leg-openings 7 at a bottom of the pants 1. The waist-opening 6 is provided along its peripheral edge with a circumferentially extending film-like elastically stretchable member 8 bonded with tension thereto.

The inner sheets 2A, 2B are contoured by upper and lower ends 2a, 2b extending in parallel to each other transversely of the pants 1 and a front and rear side portions 2c, 2d extending in parallel to each other longitudinally of the pants 1. The inner sheets 2A, 2B are formed between the front and rear side portions 2c, 2d with a cutout 9 depressed from the upper end 2a toward the lower end 2b. The rear side edge 2d of the inner sheets 2A, 2B gets nearer, describing a circular arc, to a longitudinal center line Y1 as the rear side edge 2d extends from the upper end 2a toward the lower end 2b.

The inner sheets 2A, 2B are provided in the vicinity of their bottom sides 9b with elastically stretchable members 13 transversely extending above the respective panels 5A, 5B in a manner such that these members 13 are bonded with tension to the respective inner sheets 2A, 2B and covered with portions thereof.

The panels 5A, 5B are placed in a region surrounded by the front and rear side portions 2c, 2d, the lower end 2b and the bottom side 9b of the inner sheets 2A, 2B and bonded to a surface of the sheets 2A, 2B opposed to the panels 5A, 5B.

The outer sheets 3A, 3B are contoured by upper and lower ends 3a, 3b transversely extending in parallel to each other and front and rear side edges 3c, 3d longitudinally extending in parallel to each other. The rear side edge 3d of the outer sheets 3A, 3B gets nearer, describing a circular arc, to a longitudinal center line Y2 bisecting a dimension between the front side edge 3c and the rear side edge 3d as the rear side edge 3d extends from the upper end 3a toward the lower end 3b. Surface of the outer sheets 3A, 3B opposed to the inner sheets 2A, 2B are provided along upper end 3a with a transversely extending elastic member 8 bonded thereto.

To assemble the components illustrated by FIG. 6 in the exploded perspective view and thereby to obtain the pants 1, the inner sheets 2A, 2B are placed upon each other with the respective center lines Y1 brought in line with each other and then the opposed surfaces thereof are continuously or intermittently bonded to each other along bond lines 11. These bond lines 11 extend in parallel to the cutouts 9, describing circular arcs, from the upper ends 2a toward the lower ends 2b of the sheets 2A, 2B, respectively. The portions of the bond lines 11 describing the circular arcs extend between the panels 5A, 5B and the lower ends 2b of the sheets 2A, 2B.

After the opposed surfaces of the inner sheets 2A, 2B have been bonded to each other, the respective fixed ends 4a of the side sheets 4A, 4B are partially folded back to respective inner surfaces of the side sheets 4A, 4B and these fixed ends 4a are bonded to respective outer surfaces of the sheets 2A, 2B in the vicinity of their respective bottom sides 9b. At the same time, the transversely opposite ends 4c also are bonded to the sheets 2A, 2B in the vicinity of their opposed sides 9a with the elastic members 10 being kept under tension.

The inner sheets 2A, 2B and the outer sheets 3A, 3B are placed upon one another, respectively, with the center lines Y1, Y2 of these inner and outer sheets 2A, 2B; 3A, 3B brought in line with one another, respectively. Then the inner and outer sheets 2A, 3A have their surfaces opposed to each other continuously or intermittently bonded to each other by means of bond lines 12 extending along the front and rear side portions 2c, 2d; 3c, 3d, respectively. Similarly, the inner and outer sheets 2B, 3B have their surfaces opposed to each other continuously or intermittently bonded to each other by means of bond lines 12 extending along the front and rear side portions 2c, 2d; 3c, 3d, respectively.

In the pants 1 according to this alternative embodiment, the front and rear side portions 2c, 2d of the sheets 2A, 2B have portions lying in the upper ends 2a and bonded to each other along bond lines 14. These portions bonded together provide a higher bonding strength as measured circumferentially of the pants 1 than the bonding strength which will be provided by these portions not bonded together. In this manner, there is no anxiety that the inner sheets 2A, 2B might be separated from each other as the pants 1 are put on the wearer's body and the waist-opening is circumferentially stretched.

Figure 7:
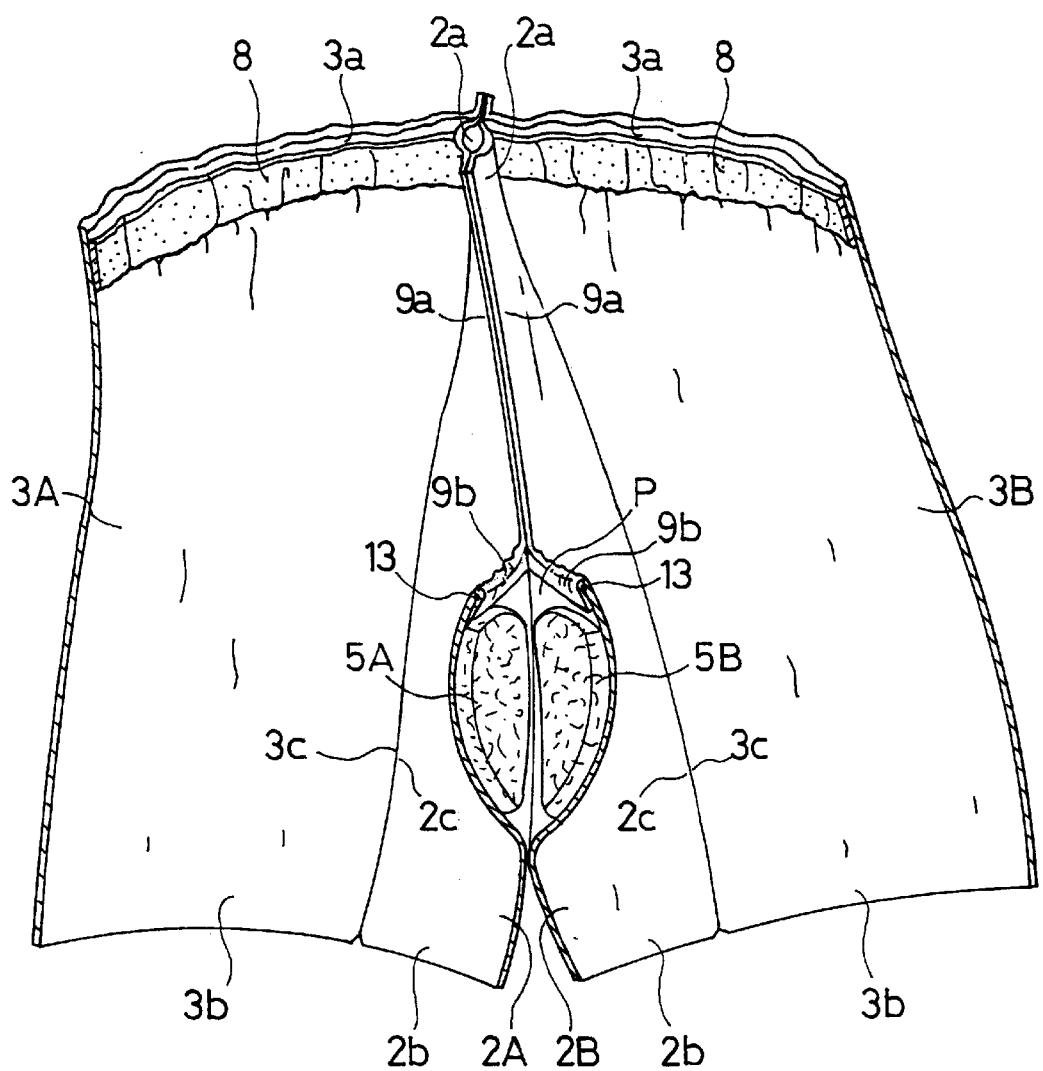
FIG. 7 is a perspective view showing the pants of FIG. 5 as viewed in a section taken along line C—C in FIG. 5.
Figure 8:
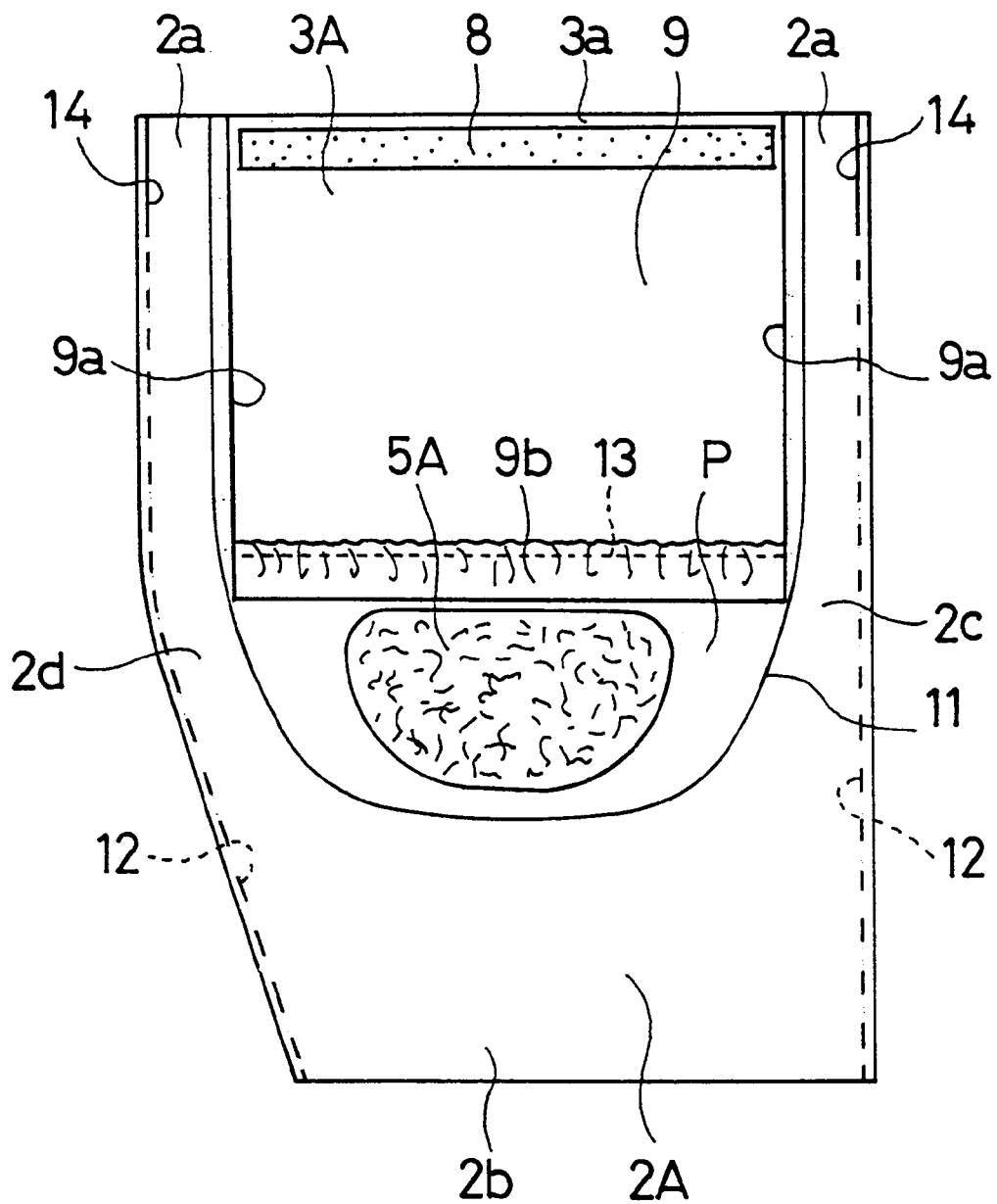
FIG. 8 is a sectional view showing the pants of FIG. 5 as taken along line D—D in FIG. 5.

FIG. 7 is a perspective view showing the pants of FIG. 5 as viewed in a section taken along line C—C in FIG. 5 and FIG. 8 is a sectional view taken along line D—D in FIG. 5. The inner sheets 2A, 2B are placed upon each other so that the respective pairs of opposed sides 9a face inwardly of the pants 1 in contact with each other. The front and rear side portions 2c, 2d of the respective inner sheets 2A, 2B face outwardly of the pants 1 in contact with the front and rear side edges 3c, 3d of the adjacent outer sheets 3A, 3B, respectively.

In the pants 1 assembled, the opposed surfaces of the inner sheets 2A, 2B extending from their bottom sides 9b to the respective bond lines 11 expand outward transversely of the pants 1 as elastic members 13 contract, resulting in formation of a pocket P opening upwardly of the pants 1.

The inner sheets 2A, 2B forming the pocket P serve as barriers of the pocket P. Excretion discharged into the pocket P is absorbed by the panels 5A, 5B lying within the pocket P. The barriers function to prevent excretion leak from occurring in the vicinity of a crotch region. The panels 5A, 5B extend substantially in vertical direction in parallel to the inner sheets 2A, 2B and, in a wearer's crotch region, are substantially less bulky than in the case of the panels 5A, 5B extending in horizontal direction. Thus, it is not apprehended that these panels 5A, 5B give the wearer a feeling of incompatibility.

The surfaces of the inner sheets 2A, 2B opposed to each other have their upper ends 2a not bonded to each other and therefore it is not apprehended that the regions of the sheets 2A, 2B extending in the vicinity of their upper ends 2a might give the wearer a feeling of stiffness even when these regions are pressed against the wearer's skin under a contractile force of the elastic members 8.

In these embodiments of the pants 1 illustrated by FIGS. 1 and 5, respectively, the sheets 2A, 2B are bonded together leaving innermost edges of the opposed sides 9a free over an extent sufficient to alleviate a stiffness of the bonded regions even when these innermost edges come in contact with the wearer's crotch. In this way, stimulation possibly experienced by the wearer's skin can be effectively alleviated.

The surfaces of the inner sheet 2A and the adjacent outer sheet 3A as well as the surfaces of the inner sheet 2B and the adjacent outer sheet 3B are bonded to one another leaving outermost edges of their front and rear sides 2c, 3c, 2d, 3d free over an extent sufficient to alleviate a stiffness of the bonded regions even when these innermost edges come in contact with the wearer's arms. In this way, stimulation possibly experienced by the wearer's skin is effectively alleviated.

An alternative embodiment is also possible such that both the front side portions 2c3c and the rear side portions 2d, 3d of the inner and outer sheets 2A, 2B; 3A, 3B get near to the respective center lines Y1, Y2, describing circular arcs or describing straight lines as these front and rear side portions extend from their upper ends 2a, 3a to their lower ends 2b, 3b.

The inner sheets 2A, 2B and/or the outer sheets 3A, 3B may be formed from a nonwoven fabric of thermoplastic fiber. The side sheets 4A, 4B also may be formed from a nonwoven fabric of thermoplastic fiber. A nonwoven fabric made porous to improve its moisture-pervious property or the nonwoven fabric formed on its sheet surface with irregularities to improve its cushioning property also may be used for this purpose. Particularly the inner sheets 2A, 2B destined to come in direct contact with the wearer's crotch are preferably formed with the material offering high liquid-permeability, moisture-permeability and softness, for example, rayon or cotton fiber containing nonwoven fabric.

It is also possible to use composite nonwoven fabric (SMS nonwoven fabric) comprising high water-resistance melt blown nonwoven fabric having opposite sheet surfaces each laminated with sheet surface of spun bond nonwoven fabric having a high strength and a high flexibility. The SMS nonwoven fabric is obtained by sandwiching the melt blown nonwoven fabric between two layers of spun bond nonwoven fabric and then bonding these melt blown nonwoven fabric and spun bond nonwoven fabric together using a technique of press working. Use of the SMS nonwoven fabric advantageously results in the pants 1 having a high strength, a high water-resistance and a comfortable touch.

The outer sheets 3A, 3B may be also formed from a nonwoven fabric which is stretchable transversely thereof or both transversely and longitudinally thereof. In this case, the elastic members 8 associated with the waist-opening provided along the upper ends 3a of the sheets 3A, 3B may be eliminated.

The elastic members 8, 10, 13 may be formed from a synthetic rubber, a natural rubber, a stretchable film containing synthetic rubber, or a spun bond nonwoven fabric or a melt blown nonwoven fabric containing synthetic rubber as a principal ingredient. It is also possible to cover the elastic members 8, 10, 13 with nonwoven fabric and to bond the elastic members with tension to said nonwoven fabric.

The elastic members 8, 10, 13 may be formed with a synthetic rubber, a natural rubber, a stretchable film containing synthetic rubber, or a spun bond nonwoven fabric or a melt blown nonwoven fabric containing synthetic rubber as a principal ingredient. It is also possible to cover the elastic members 8, 10, 13 with nonwoven fabric and to bond the elastic members with tension to said nonwoven fabric.

It is also possible to attach the elastic members 8 associated with the waist-opening to the respective outer surfaces of the outer sheets 3A, 3B. In the pants 1 assembled, it is possible to cover the exposed regions of the elastic members 8 attached to the opposed surfaces of the sheets 3A, 3B with nonwoven fabric in order to prevent the elastic members 8 from coming in contact with the wearer's skin.

The liquid-absorbent panel 5A, 5B comprises a mixture of fluff pulp and high absorption polymer grains compressed to a desired thickness and entirely covered with a water-pervious sheet such as tissue paper (not shown). Bonding of the panels 5A, 5B, the elastic members 8, 10, 13 and the sheets 2A, 2B, 3A, 3B, 4A, 4B may be carried out using suitable adhesive such as hot melt adhesive, pressure-sensitive adhesive or a fusing technique such as heat-sealing or supersonic sealing.

What is claimed is:

1. Disposable pants which comprise:
   a waist-opening at a top portion thereof, said waist-opening provided along a peripheral edge thereof with an elastic stretchability circumferentially thereof;
   a pair of leg-openings at a bottom portion thereof;
   a pair of inner sheets confronting each other, said inner sheets being contoured by upper and lower ends transversely extending in parallel to each other, and front and rear side portions longitudinally extending in parallel to each other, said pair of inner sheets also being formed between their front and rear side portions with cutouts depressed from said upper ends toward said lower ends;
   liquid-absorbent panels attached to opposed surfaces of said inner sheets; and
   a pair of outer sheets lying outside said inner sheets, said outer sheets being contoured by upper and lower ends transversely extending in parallel to each other, and front and rear side portions longitudinally extending in parallel to each other;
   opposed surfaces of said inner sheets being bonded together by means of bond lines extending in parallel to said cutouts and partially extending below said liquid-absorbent panels, and
   opposed surfaces of said inner sheets and said outer sheets being bonded together along said front and rear side portions of these sheets.

2. The pants according to claim 1, wherein the opposed surfaces of said inner sheets are bonded together along the upper ends of said inner sheets and along limited regions of said front and rear side portions lying in the vicinity of said upper ends of said inner sheets.

3. The pants according to claim 1, wherein elastically stretchable members are bonded with tension to said inner sheets along said bottom sides of said cutouts so as to extend above said liquid-absorbent panels transversely of said inner sheets.

4. The pants according to claim 1, wherein liquid-resistant side sheets are bonded to said inner sheets along said bottom sides of said cutouts so as to extend above said liquid-absorbent panels transversely of said inner sheets, said side sheets comprise a nonwoven fabric and having fixed ends transversely extending and fixed to said inner sheets, free ends extending above said fixed ends across said cutouts and transversely opposite fixed sides fixed to said inner sheets along said cutouts so as to extend longitudinally of said side sheets, said free ends being provided with elastically stretchable members bonded with tension thereto so as to extend transversely of said side sheets.

5. The pants according to claim 1, wherein at least one of said inner sheets and said outer sheets comprise a nonwoven fabric.

6. The pants according to claim 2, wherein the opposed surfaces of said inner sheets are bonded together along limited regions of said front and rear side portions lying in a vicinity of said upper ends of said inner sheets.

* * * * *